United States Patent [19]

Baudy et al.

[11] Patent Number: 5,719,153
[45] Date of Patent: Feb. 17, 1998

[54] 5H,8H-2-OXA-1,3,5,8-TETRAAZA-CYCLOPENTA[B]-NAPHTHALENE-6,7-DIONES

[75] Inventors: Reinhardt B. Baudy, Yardley; Theodore S. Sulkowski, Wayne, both of Pa.

[73] Assignee: American Home Products Corporation, Madison, N.J.

[21] Appl. No.: 692,557

[22] Filed: Aug. 6, 1996

Related U.S. Application Data

[60] Provisional application No. 60/002,356, Aug. 15, 1995.
[51] Int. Cl.$^6$ ...................... A61K 31/495; C07D 498/04
[52] U.S. Cl. ...................... 514/250; 544/345; 544/354
[58] Field of Search ...................... 544/345; 514/250

[56]  References Cited

U.S. PATENT DOCUMENTS

| | | | |
|---|---|---|---|
| 4,912,108 | 3/1990 | Jacobsen et al. | 514/250 |
| 5,109,001 | 4/1992 | Jacobsen et al. | 514/250 |

FOREIGN PATENT DOCUMENTS

| | | |
|---|---|---|
| 20260467 | 3/1988 | European Pat. Off. . |

OTHER PUBLICATIONS

Doble, *Thérapie* 50, pp. 319–337 (1995).

Primary Examiner—Emily Bernhardt
Attorney, Agent, or Firm—Arnold S. Milowsky

[57]  ABSTRACT

This invention provides compounds having the structure

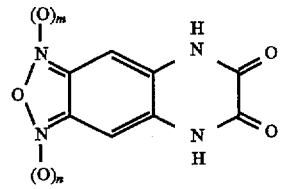

wherein
  m=0–1; and
  n=0–1 or a pharmaceutically acceptable salt thereof when m and n=0, that are useful as neuroprotective agents.

4 Claims, No Drawings

5H,8H-2-OXA-1,3,5,8-TETRAAZA-CYCLOPENTA[B]-NAPHTHALENE-6,7-DIONES

BACKGROUND OF THE INVENTION

This application claims the benefit of U.S. Provisional Application No. 60/002,356, filed Aug. 15, 1995.

This invention provides 5H,8H-2-oxa-1,3,5,8-tetraaza-cyclopenta[b]-naphthalene-6,7-diones that are useful as neuroprotective agents.

L-glutamic acid, L-aspartic acid and a number of other closely related amino acids have in common the ability to activate neurons in the central nervous system. Biochemical, electrophysiological and pharmacological studies have substantiated this and demonstrated that acidic amino acids are transmitters for the vast majority of excitatory neurons in the mammalian CNS.

Interaction with such an acidic amino acid mediated neurotransmission is considered a useful approach in the treatment of neurological and psychiatric diseases. It has been suggested that accumulation of extracellular excitatory and neurotoxic amino acids, followed by hyperstimulation of neurons, may explain the neuronal degeneration seen in neurological diseases as Parkinsonism, senile dementia, Huntingtons chorea, and deficiencies of mental and motoric performance seen after conditions of brain ischaemia, anoxia and hypoglycemia. (E. G. McGeer et al., Nature, 263, 517–9, (1976) and R. Simon et al., Science, 226, 850–2, (1984).

AMPA receptors are activated selectively by AMPA, other potent agents being quisqualic acid and L-glutamic acid. It is well known that an excitatory amino acid projection from prefrontal cortex to nucleus accumbens exists (Christie et al., J. Neurochem., 45, 477–82, (1985). Further it is known that glutamate modulates the dopaminergic transmission in the striatum (Rudolph et al., Neurochem. int., 5, 479–86, (1983) as well as the hyperactivity connected with presynaptic stimulation of the dopamine system with AMPA in nucleus accumbens.

DESCRIPTION OF THE INVENTION

This invention provides compounds useful as neuroprotective agents, having the structure

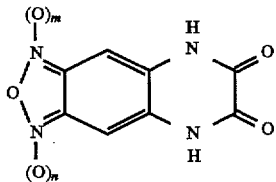

wherein m=0–1, and n=0–1 or a pharmaceutically acceptable salt thereof when m and n=0.

The pharmaceutically acceptable salts are those derived from such acids such as as: hydrochloric, hydrobromic, phosphoric, nitric, sulfuric, and similarly known acceptable acids.

The compounds of the present invention may be prepared via a variety of routes as illustrated in FIG. 1 using conventional methods and starting materials whose preparation is described in the literature.

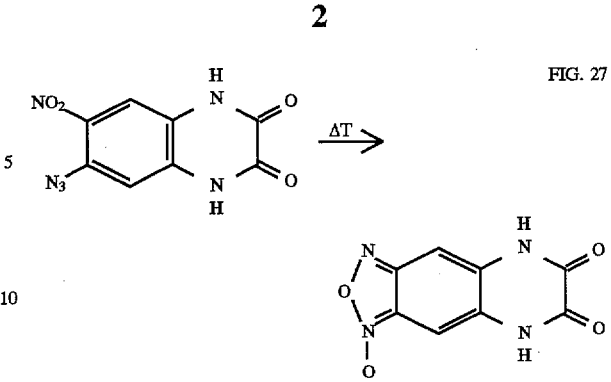

FIG. 27

The starting 6-azido-2,3-dihydroxy-7-nitroquinoxaline can be prepared according to the method of Honore T. et. al. (EP 0260467A2).

A representative compound of this invention was evaluated in a standard pharmacological test procedure to determine its ability to displace [$^3$H]-α-amino-3-hydroxy-5-methylisoxazole-4-propionic acid (AMPA) from its binding site on rat forebrain membranes as described in a modified assay by D. E. Murphy, E. W. Snowhill and M. Williams (Characterization of quisqualate recognition sites in rat brain tissue using DL-[$^3$H]α-amino-3-hydroxy-5-methylisoxazole-4-propionic acid (AMPA) and a filtration assay, Neurochemical Research, Vol. 12, No.9, 1987, pp. 775–782). Briefly, rats were decapitated and their forebrains (whole brain minus brain stem and cerebella) were homogenized in a volume (ml) of ice cold 0.32M sucrose equivalent to 15 times the forebrain weight (gram). The homogenate was centrifuged at 1,000 g for 10 minutes and the supernatant was recentrifuged at 20,000 g for 20 min. The pellet was resuspended in ice-cold distilled water and centrifuged at 8,000 g for 20 min. The supernatant and buffy coat were centrifuged at 48,000 g for 10 min. The pellet was then resuspended in the original volume of ice-cold 50 mmolar TRIS HCl (pH 7.4) and centrifuged at 48,000 g for 10 min. The pellet was resuspended in 50 mmolar TRIS HCl containing 0.04% Triton X-100 and the homogenate was incubated at 37° C. for 30 min. The homogenate was then centrifuged at 48,000 g for 10 min. The pellet was resuspended in 50 mmolar TRIS buffer and centrifuged at 48,000 g for 10 min for a total of three washes and the pellet was frozen at −70° C. for subsequent use in the binding test procedure. For the binding test procedure, the pellet was resuspended in twice the original volume of ice-cold 50 mmolar TRIS HCl. Triplicate samples (100 µl) of the membrane homogenate containing between 300 to 500 µg protein/ml of homogenate were incubated at 4° C. for 1 hr with 5 nmolar [$^3$H]AMPA (New England Nuclear; specific activity ~27 Ci/mmole), one of various test solutions, 100 mmolar KSCN and buffer to a final incubation volume of 2 ml. One mmolar L-glutamic acid and TRIS buffer were substituted for the test solution in separate triplicates to determine non-specific binding and total binding, respectively. The tissue homogenates were then filtered under vacuum through Whatman GF/B glass fiber filters and rinsed with three 2 ml rinses of ice cold TRIS buffer. The filters were placed into individual glass scintillation vials and prepared for counting using conventional liquid scintillation spectroscopy. The displacement activity of the compounds may be shown by determining the $IC_{50}$ value which represents the concentration (mg/mL) that causes a displacement of 50% of the specific binding of [$^3$H]-AMPA.

The results obtained for a representative compound of this invention in the standard pharmacological test procedure described above, are as follows:

| Compound | [$^3$H]-AMPA binding (IC$_{50}$) |
|---|---|
| Example 1 | 7.6 μM |

The results obtained in this standard pharmacological test procedure demonstrate that the compounds this invention possess high affinities for the AMPA receptor, and are therefore useful as neuroprotective agents. As such the compounds of this invention may be administered to a mammal in the treatment of chronic and acute neurodegenerative disorders such as cerebral ischemia, convulsions, traumatic brain injury, and epilepsy. Specific applications also include therapy of senile dementia Alzheimer-type, parkinsonian dementia complex and other dominant or recessive spinocerebellar degenerations where AMPA antagonists prevent or retard the progression of the disease.

When administered for the treatment of the above disease states, the compounds of this invention can be administered to a mammal orally, parenterally, intranasally, intrabronchially, transdermally, intravaginally, or rectally.

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage to be used in the treatment of a specific psychosis must be subjectively determined by the attending physician. The variables involved include the specific psychosis or state of anxiety or depression and the size, age and response pattern of the patient. Based on the results obtained in the standard pharmacological test procedures, projected oral daily dosages of active compound would be 1–500 mg/kg and preferably between 1–100 mg/kg. Projected intravenous daily dosages would be 0.1–75 mg/kg and preferably between 0.1–25 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following example illustrates the production of a representative compound of this invention.

EXAMPLE 1

1-Oxy-5H,8H-2-oxa-1,3,5,8-tetraaza-cyclopenta[b]naphthalene-6,7-dione

The starting 6-azido-2,3-dihydroxy-7-nitroquinoxaline (500 mg, 2 mmole) was heated to reflux in toluene (50 mL) for four hours. The resulting suspension was cooled to ambient temperature, filtered and washed with toluene (30 mL), followed by diethylether (50 mL). The filtered material was dried in vacuo at 60° C. for three hours to yield 350 mg of the title compound, m.p.>300° C. (Decomposition).

Elemental Analysis for: $C_8H_4N_4O_4$

Calcd: C, 43.65; H, 1.83; N, 25.45.

Found: C, 43.68; H, 1.79; N, 26.07.

What is claimed is:

1. A compound having the structure

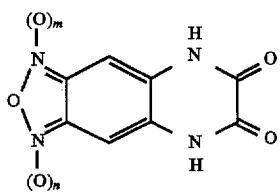

wherein m=0–1; and n=0–1 or a pharmaceutically acceptable salt thereof when m and n=0.

2. The compound of claim 1 which is 1-Oxy-5H,8H-2-oxa-1,3,5,8-tetraaza-cyclopenta[b]naphthalene-6,7-dione.

3. A pharmaceutical composition which comprises a compound of the structure

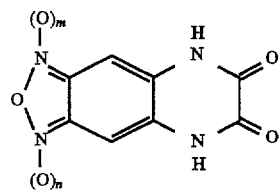

wherein m=0–1; and n=0–1 or a pharmaceutically acceptable salt thereof when m and n=0, and a pharmaceutical carrier.

4. A method of treating cerebral ischemia, convulsions, traumatic brain injury, or epilepsy in a mammal in need thereof which comprises administering to said mammal, an effective amount of a compound of the structure

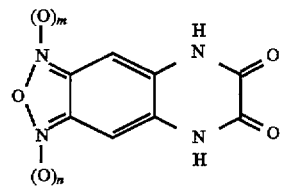

wherein m=0–1; and n=0–1 or a pharmaceutically acceptable salt thereof when m and n=0.

* * * * *